(12) United States Patent
Umemura et al.

(10) Patent No.: US 10,295,479 B2
(45) Date of Patent: May 21, 2019

(54) BOARD INSPECTION APPARATUS

(71) Applicant: CKD Corporation, Aichi (JP)

(72) Inventors: Nobuyuki Umemura, Aichi (JP); Akira Kato, Aichi (JP); Tsuyoshi Ohyama, Aichi (JP); Norihiko Sakaida, Aichi (JP)

(73) Assignee: CKD Corporation, Aichi (JP)

( * ) Notice: Subject to any disclaimer, the term of this patent is extended or adjusted under 35 U.S.C. 154(b) by 216 days.

(21) Appl. No.: 15/385,999

(22) Filed: Dec. 21, 2016

(65) Prior Publication Data
US 2017/0276617 A1 Sep. 28, 2017

(30) Foreign Application Priority Data

Mar. 22, 2016 (JP) .................................. 2016-056511

(51) Int. Cl.
| | |
|---|---|
| *G01N 21/956* | (2006.01) |
| *G01N 21/95* | (2006.01) |
| *H04N 5/225* | (2006.01) |
| *H04N 5/247* | (2006.01) |

(52) U.S. Cl.
CPC ....... *G01N 21/956* (2013.01); *G01N 21/9501* (2013.01); *H04N 5/2256* (2013.01); *H04N 5/247* (2013.01); *G01N 2021/95646* (2013.01); *G01N 2201/12* (2013.01)

(58) Field of Classification Search
None
See application file for complete search history.

(56) References Cited

U.S. PATENT DOCUMENTS 5,450,204 A * 9/1995 Shigeyama ...... G01N 21/95607
356/394
2017/0276924 A1* 9/2017 Chan .................... G02B 21/365

FOREIGN PATENT DOCUMENTS

JP 2006-184022 A 7/2006
JP 2006184022 A * 7/2006

* cited by examiner

*Primary Examiner* — Christopher G Findley
(74) *Attorney, Agent, or Firm* — Osha Liang LLP

(57) ABSTRACT

A board inspection apparatus is disclosed, which includes one surface-side irradiator that irradiates a first area on a surface side of a board with first light, a surface-side camera that takes an image of the first area, one rear face-side irradiator that irradiates a second area on a rear face side of the board with second light, a rear face-side camera that takes an image of the second area; and a controller that inspects the first area based on image data obtained from the surface-side camera and the second area based on image data obtained from the rear face-side camera.

19 Claims, 6 Drawing Sheets

BOARD INSPECTION APPARATUS

BACKGROUND OF THE INVENTION

Technical Field

The present disclosure relates to a board inspection apparatus for inspecting both a surface and a rear face of a printed circuit board or the like.

Background Art

A printed circuit board with electronic components mounted on both a surface and a rear face thereof generally has electrode patterns formed on both a surface and a rear face of a base substrate that is formed from a glass epoxy resin, and resist films provided to protect these electrode patterns.

In a production line for mounting electronic components on such a printed circuit board, a procedure first prints solder paste at predetermined positions on both the surface and the rear face of the printed circuit board (solder printing process). The procedure subsequently applies an adhesive at the predetermined positions on both the surface and the rear face of the printed circuit board (adhesive applying process). The procedure subsequently mounts electronic components on both the surface and the rear face of the printed circuit board (mounting process). The electronic components are temporarily fastened by the viscosity of the solder paste or by means of the adhesive. The procedure then introduces the printed circuit board into a reflow furnace for soldering (reflow process).

For example, a board inspection apparatus configured to perform an inspection for the printing state of solder paste prior to mounting of components (solder printing inspection apparatus) or a board inspection apparatus configured to perform an inspection with regard to a printed circuit board after mounting of components (mounting inspection apparatus) may be provided in this production line.

An inspection apparatus configured to perform an inspection simultaneously with regard to both the surface and the rear face of the printed circuit board is known as this board inspection apparatus.

In the board inspection apparatus configured to perform an inspection simultaneously with regard to both the surface and the rear face, however, there is a possibility that part of light emitted toward one face side of the printed circuit board is transmitted through a hole pierced through the printed circuit board or through the glass epoxy resin of the base substrate and is leaked to the other face side of the printed circuit board. As a result, leakage of light from one face side is likely to affect and decrease the inspection accuracy with regard to inspection of the other face side of the printed circuit board.

A recently proposed inspection apparatus places illumination units at offset positions on the surface side and on the rear face side of the printed circuit board or performs an inspection simultaneously with regard to both the surface side and the rear face side of the printed circuit board that are irradiated with the light of the same color (as described in, for example, Patent Literature 1).

CITATION LIST

Patent Literature

PTL 1: JP 2006-184022A

SUMMARY OF THE INVENTION

Even in the configuration of Patent Literature 1 described above, however, simultaneous light emission on both the surface side and the rear face side of the printed circuit board is likely to cause a slight leakage of light to the opposite side. There are thus still concerns about the effect on the inspection accuracy.

For example, in a configuration that performs three-dimensional measurement (inspection) based on a difference between luminance values of a plurality of image data taken with patterned light having different phases, for example, three-dimensional measurement by the phase shift method, even a slight leakage of even the light of the same color from the other face side of the printed circuit board is likely to provide a significant effect on the inspection accuracy with regard to inspection of one face side of the printed circuit board.

A configuration that performs, for example, inspection of the rear face side of the printed circuit board after completion of inspection of the surface side of the printed circuit board is, on the other hand, likely to increase the inspection time.

For example, in the case where there is a need to take an image of a predetermined inspection area a plurality of times, as in the case of three-dimensional measurement by the phase shift method, such a need is likely to cause a remarkable increase in the inspection time.

By taking into account the circumstances described above, a board inspection apparatus according to one or more embodiments improves the inspection accuracy with regard to double-sided inspection of a board and increase the speed of inspection.

The following describes each of various aspects of the invention. Functions and advantageous effects that are characteristic of each of the aspects of the invention are also described as appropriate.

Aspect 1: There is provided a board inspection apparatus configured to perform an inspection with regard to both a surface and a rear face of a board. The board inspection apparatus comprises at least one surface-side irradiator configured to irradiate a predetermined inspection area on a surface side of the board with predetermined light; a surface-side imaging unit configured to take an image of the predetermined inspection area on the surface side of the board that is irradiated with the predetermined light; at least one rear face-side irradiator configured to irradiate a predetermined inspection area on a rear face side of the board with predetermined light; a rear face-side imaging unit configured to take an image of the predetermined inspection area on the rear face side of the board that is irradiated with the predetermined light; and an inspection unit configured to perform an inspection with regard to the predetermined inspection area on the surface side of the board, based on a plurality of image data obtained by an image acquisition process with regard to the predetermined inspection area on the surface side of the board performed by the surface-side irradiator and the surface-side imaging unit, and configured to perform an inspection with regard to the predetermined inspection area on the rear face side of the board, based on a plurality of image data obtained by an image acquisition process with regard to the predetermined inspection area on the rear face side of the board performed by the rear face-side irradiator and the rear face-side imaging unit. A specific process is carried out to alternately perform one imaging process among a plurality of imaging processes with regard to the predetermined inspection area by the surface-side imaging unit and one imaging process among a plurality of imaging processes with regard to the predetermined inspection area by the rear face-side imaging unit. The specific process is configured to start emission of light from the surface-side irradiator and stop emission of light from the rear face-side irradiator, so as to perform one imaging process among the plurality of imaging processes with regard to the predetermined inspection area by the surface-side imaging unit, and subsequently stop emission of light from the surface-side irradiator and start emission of light from the rear face-side irradiator, so as to perform one imaging process among the plurality of imaging processes with regard to the predetermined inspection area by the rear face-side imaging unit. The specific process is also configured to start emission of light from the rear face-side irradiator and stop emission of light from the surface-side irradiator, so as to perform one imaging process among the plurality of imaging processes with regard to the predetermined inspection area by the rear face-side imaging unit, and subsequently stop emission of light from the rear face-side irradiator and start emission of light from the surface-side irradiator, so as to perform one imaging process among the plurality of imaging processes with regard to the predetermined inspection area by the surface-side imaging unit.

The configuration of the aspect 1 described above stops emission of light on the rear face side (or on the surface side) during an imaging period with regard to the surface side (or with regard to the rear face side) of the board. This configuration enables image data of the high accuracy to be obtained without causing leakage of light to the surface side (or to the rear face side). As a result, this configuration improves the inspection accuracy with regard to double-sided inspection of the board.

Additionally, this aspect is configured to perform an imaging process with regard to the surface side (or with regard to the rear face side) of the board and subsequently perform an imaging process with regard to the rear face side (or with regard to the surface side) of the board. Accordingly, alternately repeating the imaging process with regard to the surface side of the board and the imaging process with regard to the rear face side of the board enables the image acquisition process (a plurality of imaging processes) with regard to a predetermined inspection area on the surface side of the board and the image acquisition process (a plurality of imaging processes) with regard to a predetermined inspection area on the rear face side of the board to be performed at the same time.

This configuration increases the inspection speed with regard to double-sided inspection of the board, compared with a configuration that performs, for example, the image acquisition process (a plurality of imaging processes) with regard to the predetermined inspection area on the rear face side of the board after completion of the image acquisition process (a plurality of imaging processes) with regard to the predetermined inspection area on the surface side of the board.

As a result, this configuration improves the inspection accuracy with regard to double-sided inspection of the board and increases the speed of inspection.

Aspect 2: In the board inspection apparatus described in the above aspect 1, the specific process may cause the rear face-side imaging unit to perform the imaging process during a time period when the surface-side imaging unit is not allowed to perform the imaging process (for example, a time period in which imaging is functionally impossible, such as a data transfer period by the surface-side imaging unit) or during a time period when the surface-side imaging unit does not perform the imaging process (for example, a time period relatively determined due to another cause, such as transfer of a grid by the surface-side irradiator or a switchover period). The specific process may also cause the surface-side imaging unit to perform the imaging process during a time period when the rear face-side imaging unit is not allowed to perform the imaging process (for example, a time period in which imaging is functionally impossible, such as a data transfer period by the rear face-side imaging unit) or during a time period when the rear face-side imaging unit does not perform the imaging process (for example, a time period relatively determined due to another cause, such as transfer of a grid by the rear face-side irradiator or a switchover period).

The configuration of the aspect 2 described above utilizes, for example, the time period when the imaging process is not allowed to be performed by one of the imaging units (for example, the surface-side imaging unit), to perform the imaging process by the other imaging unit (for example, the rear face-side imaging unit).

For example, after termination of the imaging process by one of the imaging units (for example, the surface-side imaging unit), the imaging process by the other imaging unit (for example, the rear face-side imaging unit) may be performed during data transfer by the one imaging unit.

This configuration enables the image acquisition process (a plurality of imaging processes) with regard to the predetermined inspection area on the other face side (for example, the rear face side) of the board to be performed during a minimum time period required for the image acquisition process (a plurality of imaging processes) by one of the imaging units (for example, the surface-side imaging unit) with regard to the predetermined inspection area on one face side (for example, the surface side) of the board. As a result, this configuration increases the inspection speed with regard to double-sided inspection of the board.

Aspect 3: In the board inspection apparatus described in the above aspect 1 or in the above aspect 2, the surface-side irradiator and the surface-side imaging unit may be driven and controlled independently of the rear face-side irradiator and the rear face-side imaging unit, and the rear face-side irradiator and the rear face-side imaging unit may be driven and controlled independently of the surface-side irradiator and the surface-side imaging unit. The image acquisition process with regard to the predetermined inspection area on the surface side of the board and the image acquisition process with regard to the predetermined inspection area on the rear face side of the board may be allowed to be performed independently of each other. The specific process may be carried out when the image acquisition process (the processing period of the image acquisition process) with regard to the predetermined inspection area on the surface side of the board is at least partly overlapped with the image acquisition process (the processing period of the image acquisition process) with regard to the predetermined inspection area on the rear face side of the board.

The configuration of the above aspect 3 enables inspection with regard to the surface side of the board and inspection with regard to the rear face side of the board to be performed independently of each other, thus improving the efficiency of inspection.

In this configuration, however, the inspection period of the surface of the board may be overlapped with the inspection period of the rear face of the board (i.e., the processing period of the image acquisition process with regard to the surface of the board may be overlapped with the processing period of the image acquisition process with regard to the rear face of the board). Accordingly, the functions and the advantageous effects of the above aspect 1 or the like are more advantageous in this configuration.

In the configuration of this aspect that the surface-side irradiator and the surface-side imaging unit are driven and controlled independently of the rear face-side irradiator and the rear face-side imaging unit and that the rear face-side irradiator and the rear face-side imaging unit are driven and controlled independently of the surface-side irradiator and the surface-side imaging unit, consistently carrying out the specific process described in the above aspect 1 is likely to decrease the efficiency of inspection, for example, to provide a standby time in the course of setting inspection areas respectively on the surface and the rear face of the board.

The configuration of this aspect, on the other hand, carries out the specific process described above only when the image acquisition process with regard to the predetermined inspection area on the surface side of the board is at least partly overlapped with the image acquisition process with regard to the predetermined inspection area on the rear face side of the board. This configuration accordingly suppresses reduction in the efficiency of inspection.

Aspect 4: In the board inspection apparatus described in any one of the above aspects 1 to 3, at least one of the surface-side irradiator and the rear face-side irradiator may be configured to emit patterned light having a light intensity distribution of a stripe shape as the predetermined light. The inspection unit may be configured to perform three-dimensional measurement by a phase shift method, based on a plurality of image data taken with the patterned light of different phases.

In the case where three-dimensional measurement is performed by the phase shift method with regard to both the surface and the rear face of the board, by taking into account, for example, a potential leakage of light from the opposite side, a conventional configuration takes all a plurality of (for example, four) image data with regard to a predetermined inspection area with patterned light having the phase varied to a plurality of different phases while sequentially shifting (or switching over) a grid of the surface-side irradiator and subsequently takes all a plurality of (for example, four) image data with regard to a predetermined inspection area with patterned light having the phase varied to a plurality of different phases while sequentially shifting (or switching over) a grid of the rear face-side irradiator.

The configuration of the above aspect 4, on the other hand, enables a plurality of imaging processes on the other face side (for example, the rear face side) of the board to be performed for the purpose of three-dimensional measurement by the phase shift method, between a plurality of imaging processes on one face side (for example, the surface side) of the board performed for the purpose of three-dimensional measurement by the phase shift method.

This configuration accordingly enables all (for example, four) image data required for the three-dimensional measurement by the phase shift method to be obtained with regard to a predetermined inspection area on the other face side (for example, the rear face side) of the board, while obtaining all (for example, four) image data required for the three-dimensional measurement by the phase shift method with regard to a predetermined inspection area on one face side (for example, the surface side) of the board. As a result, this configuration increases the inspection speed with regard to double-sided inspection of the board.

Aspect 5: In the board inspection apparatus described in any one of the above aspects 1 to 4, the board may be either a printed circuit board on which solder paste is printed or a wafer substrate on which a solder bump is formed.

The configuration of the above aspect 5 serves to perform an inspection for solder paste printed on the printed circuit board or an inspection for a solder bump formed on the wafer substrate. Accordingly the functions and the advantageous effects of each of the above aspects may be provided in inspection of solder paste or in inspection of solder bumps. This allows for quality determination of solder printing or solder bump formation with the high accuracy. As a result, this configuration improves the inspection accuracy and increases the inspection speed with regard to inspection of solder printing or with regard to inspection of solder bumps.

DETAILED DESCRIPTION

The following describes one embodiment with reference to the drawings. First, the configuration of a printed circuit board as an inspection object is described in detail. According to this embodiment, the inspection object is a double-layer board (double-sided board) having electronic components mounted on both a surface and a rear face thereof.

Figure 2:
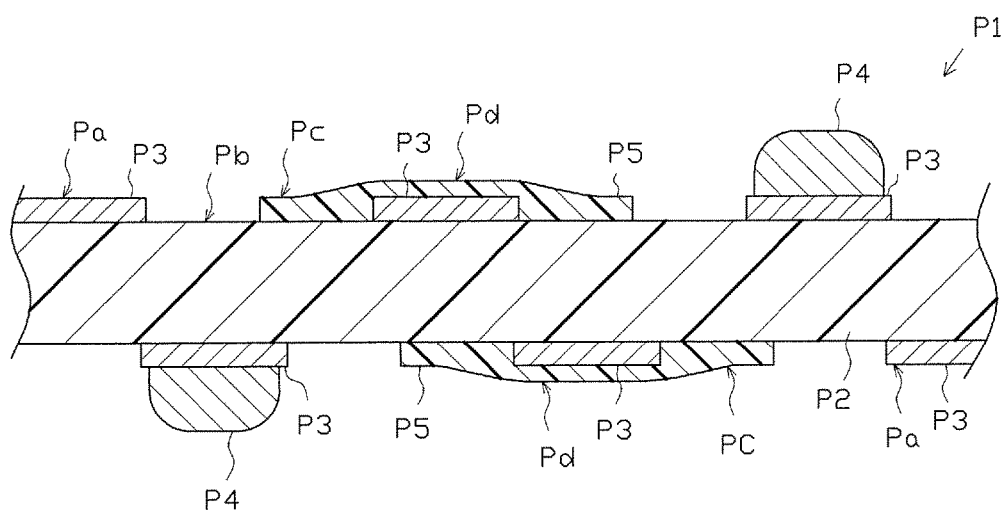
FIG. 2 is a partly enlarged sectional view illustrating an example of a printed circuit board.

As shown in FIG. 2, a printed circuit board P1 has electrode patterns P3 that are formed from a copper foil and are provided on both a surface and a rear face of a base substrate P2 that is a flat plate type and is formed from, for example, a glass epoxy resin. Additionally, solder paste P4 that is a measurement object is printed and formed on specific regions (for example, lands and pads) of the electrode patterns P3. An area in which the solder paste P4 is printed is called "solder printed area". A remaining part other than the solder printed area is generally called "background area". This background area includes an area in which the electrode pattern P3 is exposed (shown by a reference sign Pa), an area in which the base substrate P2 is exposed (shown by a reference sign Pb), an area in which the base substrate P2 is coated with a resist film P5 (shown by a reference sign Pc), and an area in which the electrode pattern P3 is coated with the resist film P5 (shown by a reference sign Pd). Both the surface and the rear face of the printed circuit board P1 are coated with the resist film P5, in order to prevent the solder paste P4 from adhering to any remaining part other than a specified wiring area.

Figure 1:
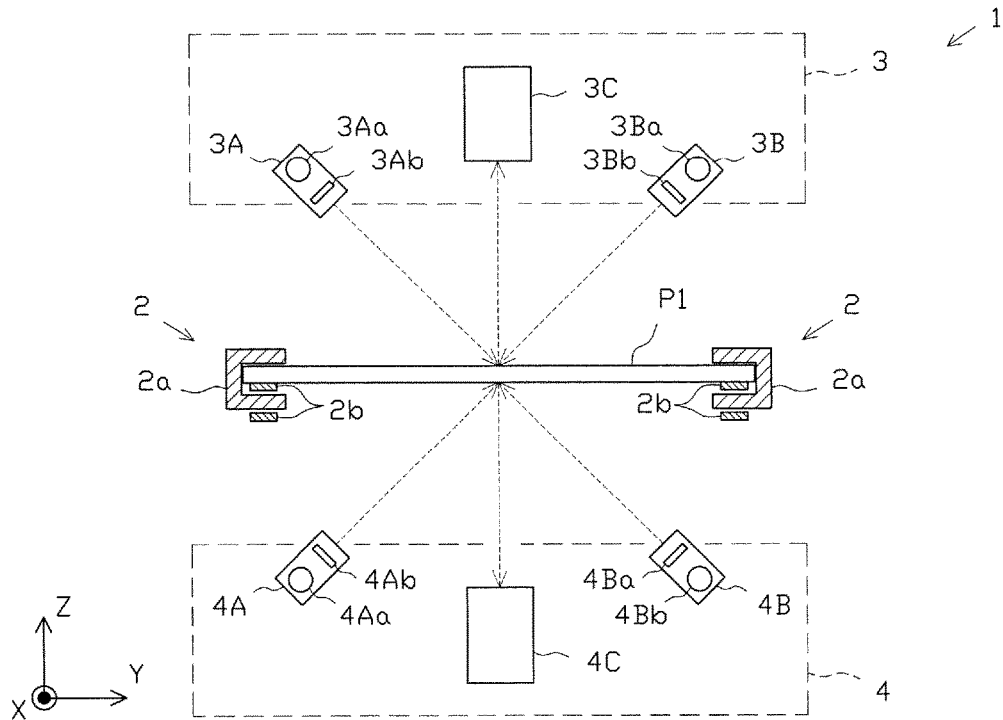
FIG. 1 is a schematic configuration diagram schematically illustrating a board inspection apparatus according to one or more embodiments of the invention.

Next, the configuration of a board inspection apparatus 1 configured to perform an inspection of the printed circuit board P1 is described below in detail. The board inspection apparatus 1 according to this embodiment is used as a solder printing inspection apparatus configured to perform an inspection for the printing state of the solder paste P4 at a stage prior to mounting of electronic components. FIG. 1 is a schematic configuration diagram schematically illustrating the board inspection apparatus 1 according to one or more embodiments of the invention.

As shown in FIG. 1, the board inspection apparatus 1 includes a conveying mechanism 2 configured to, for example, convey and position the printed circuit board P1, an upper face inspection unit 3 configured to perform an inspection with regard to an the upper face (surface) side of the printed circuit board P1, a lower face inspection unit 4 configured to perform an inspection with regard to a lower face (rear face) side of the printed circuit board P1, and a control device 6 (shown in FIG. 3) configured to perform various controls, image processing and arithmetic processing in the board inspection apparatus 1, for example, drive control of the conveying mechanism 2 and both the inspection units 3 and 4. According to this embodiment, the control device 6 serves as the inspection unit or a controller.

The conveying mechanism 2 includes a pair of conveying rails 2a arranged along a conveying direction of the printed circuit board P1, endless conveyor belts 2b provided to be rotatable relative to the respective conveying rails 2a, drive means (not shown) such as motors configured to drive the respective conveyor belts 2b, and a chuck mechanism (not shown) configured to locate the printed circuit board P1 at a predetermined position. The conveying mechanism 2 is driven and controlled by the control device 6.

The above configuration causes the printed circuit board P1 carried into the board inspection apparatus 1 to be placed on the conveyor belts 2b, while respective side edges of the printed circuit board P1 in a width direction that is perpendicular to the conveying direction are inserted into the respective conveying rails 2a. The conveyor belts 2b subsequently start operation to convey the printed circuit board P1 to a predetermined inspection position. When the printed circuit board P1 reaches the inspection position, the conveyor belts 2b are stopped and the chuck mechanism is operated. The conveyor belts 2b are pressed up by the operation of this chuck mechanism, so that the respective side edges of the printed circuit board P1 are placed between the conveyor belts 2b and the upper side portions of the conveying rails 2a. This causes the printed circuit board P1 to be located and fixed at the inspection position. After termination of inspection, the fixation by the chuck mechanism is released, and the conveyor belts 2b start operation. This causes the printed circuit board P1 to be carried out of the board inspection apparatus 1. The configuration of the conveying mechanism 2 is naturally not limited to the configuration of this embodiment described above, but any other configuration may be employed for the conveying mechanism 2.

The upper face inspection unit 3 is provided above the conveying rails 2a (i.e., the conveying path of the printed circuit board P1). The lower face inspection unit 4 is provided below the conveying rails 2a (i.e., the conveying path of the printed circuit board P1).

The upper face inspection unit 3 includes a first upper face inspection illumination device 3A and a second upper face inspection illumination device 3B provided as the surface-side irradiator configured to irradiate a predetermined inspection area on the upper face of the printed circuit board P1 with a predetermined stripe pattern for three-dimensional measurement emitted obliquely downward (patterned light having a stripe-shaped light intensity distribution), an upper face inspection camera 3C provided as the surface-side imaging unit configured to take an image of the predetermined inspection area on the upper face of the printed circuit board P1 from immediately above the predetermined inspection area, an X-axis moving mechanism 3D (shown in FIG. 3) configured to allow for the move in an X-axis direction, and a Y-axis moving mechanism 3E (shown in FIG. 3) configured to allow for the move in a Y-axis direction. The upper face inspection unit 3 is driven and controlled by the control device 6. The "inspection area" herein denotes one area among a plurality of areas set in advance on the upper face (surface) of the printed circuit board P1, based on the size of an imaging view (imaging range) of the upper face inspection camera 3C specified as one unit.

The control device 6 drives and controls the X-axis moving mechanism 3D and the Y-axis moving mechanism 3E, so as to move the upper face inspection unit 3 to a position above an arbitrary inspection area on the upper face of the printed circuit board P1 that is located and fixed at the inspection position. The upper face inspection unit 3 is successively moved to each of a plurality of inspection areas set on the upper face of the printed circuit board P1 and performs an inspection with regard to each inspection area. This configuration accordingly performs an inspection for the entire upper face of the printed circuit board P1.

The first upper face inspection illumination device 3A includes a light source 3Aa configured to emit predetermined light and a grid plate 3Ab configured to convert the light emitted from the light source 3Aa into a stripe pattern. The first upper face inspection illumination device 3A is driven and controlled by the control device 6. The light emitted from the light source 3Aa is introduced to a condenser lens (not shown) to be converted into parallel light and is subsequently introduced via the grid plate 3Ab to a projection lens (not shown) to be projected as a stripe pattern onto the printed circuit board P1.

The grid plate 3Ab has such a configuration that linear translucent portions that allow for transmission of light and linear light shielding portions that intercept light are arranged alternately in a predetermined direction perpendicular to the optical axis of the light source 3Aa. This configuration enables a stripe pattern having a light intensity distribution in a square wave form or in a trapezoidal wave form to be projected onto the printed circuit board P1. According to this embodiment, the direction of stripes in the projected stripe pattern is parallel to the X-axis direction and is perpendicular to the Y-axis direction.

The stripe pattern may not be in a perfect square wave form, since the light passing through the grid plate 3Ab is generally not the perfectly parallel light and a halftone range is likely to arise on a boundary between a "bright area" and a "dark area" of the stripe pattern, due to the diffraction effect or the like on a boundary between the light translucent portion and the light shielding portion.

A steep luminance slope of the halftone range on the boundary between the "bright area" and the "dark area" provides a stripe pattern having a light intensity distribution in a square wave form. A gentle luminance slope of the halftone range, on the other hand, provides a stripe pattern having a light intensity distribution in a trapezoidal wave form. This may, however, depend on the configuration of the grid plate 3Ab, for example, the intervals of the arrangement of the light translucent portions and the light shielding portions.

Additionally, the first upper face inspection illumination device 3A includes drive means (not shown) such as a motor provided to move the grid plate 3Ab. The control device 6 drives and controls this drive means, so as to continuously move the grid plate 3Ab at a constant speed in the predetermined direction perpendicular to the optical axis of the light source 3Aa. This enables the stripe pattern to be projected on the printed circuit board. P1 such as to be shifted along the Y-axis direction.

The second upper face inspection illumination device 3B includes a light source 3Ba configured to emit predetermined light and a grid plate 3Bb configured to convert the light emitted from the light source 3Ba into a stripe pattern. The second upper face inspection illumination device 3B is driven and controlled by the control device 6. The configuration of the second upper face inspection illumination device 3B (for example, the configuration involved in the light source 3Ba and the grid plate 3Bb) is similar to the configuration of the first upper face inspection illumination device 3A described above, so that its detailed description is omitted.

The upper face inspection camera 3C includes, for example, a lens and an imaging element. According to this embodiment, a CCD sensor is employed as the imaging element.

The upper face inspection camera 3C is driven and controlled by the control device 6. For example, the control device 6 performs an imaging process using the upper face inspection camera 3C in synchronism with the moving process of the grid plate 3Ab or 3Bb, in response to a signal from an encoder (not shown) provided in the drive means of the grid plate 3Ab or 3Bb.

Image data taken by the upper face inspection camera 3C is converted into a digital signal in the upper face inspection camera 3C, is transferred in the form of the digital signal to the control device 6, and is stored into an image data storage unit 24 described later. The control device 6 performs, for example, image processing and arithmetic processing as described later, based on the image data.

Like the upper face inspection unit 3 described above, the lower face inspection unit 4 includes a first lower face inspection illumination device 4A and a second lower face inspection illumination device 4B provided as the rear face-side irradiator configured to irradiate a predetermined inspection area on the lower face of the printed circuit board P1 with a predetermined stripe pattern for three-dimensional measurement emitted obliquely upward (patterned light having a stripe-shaped light intensity distribution), a lower face inspection camera 4C provided as the rear face-side imaging unit configured to take an image of the predetermined inspection area on the lower face of the printed circuit board P1 from immediately below the predetermined inspection area, an X-axis moving mechanism 4D (shown in FIG. 3) configured to allow for the move in the X-axis direction, and a Y-axis moving mechanism 4E (shown in FIG. 3) configured to allow for the move in the Y-axis direction. The lower face inspection unit 4 is driven and controlled by the control device 6. The "inspection area" herein denotes one area among a plurality of areas set in advance on the lower face (rear face) of the printed circuit board P1, based on the size of an imaging view (imaging range) of the lower face inspection camera 4C specified as one unit.

The control device 6 drives and controls the X-axis moving mechanism 4D and the Y-axis moving mechanism 4E, so as to move the lower face inspection unit 4 to a position below an arbitrary inspection area on the lower face of the printed circuit board P1 that is located and fixed at the inspection position. The lower face inspection unit 4 is successively moved to each of a plurality of inspection areas set on the lower face of the printed circuit board P1 and performs an inspection with regard to each inspection area. This configuration accordingly performs an inspection for the entire lower face of the printed circuit board P1.

The first lower face inspection illumination device 4A includes a light source 4Aa configured to emit predetermined light and a grid plate 4Ab configured to convert the light emitted from the light source 4Aa into a stripe pattern. The first lower face inspection illumination device 4A is driven and controlled by the control device 6. The configuration of the first lower face inspection illumination device 4A (for example, the configuration involved in the light source 4Aa and the grid plate 4Ab) is similar to the configuration of the first upper face inspection illumination device 3A described above, so that its detailed description is omitted.

The second lower face inspection illumination device 4B includes a light source 4Ba configured to emit predetermined light and a grid plate 4Bb configured to convert the light emitted from the light source 4Ba into a stripe pattern. The second lower face inspection illumination device 4B is driven and controlled by the control device 6. The configuration of the second lower face inspection illumination device 4B (for example, the configuration involved in the light source 4Ba and the grid plate 4Bb) is similar to the configuration of the first upper face inspection illumination device 3A described above, so that its detailed description is omitted.

The lower face inspection camera 4C includes, for example, a lens and an imaging element. According to this embodiment, a CCD sensor is employed as the imaging element. The configuration of the lower face inspection camera 4C is similar to the configuration of the upper face inspection camera 3C described above, so that its detailed description is omitted.

Figure 3:
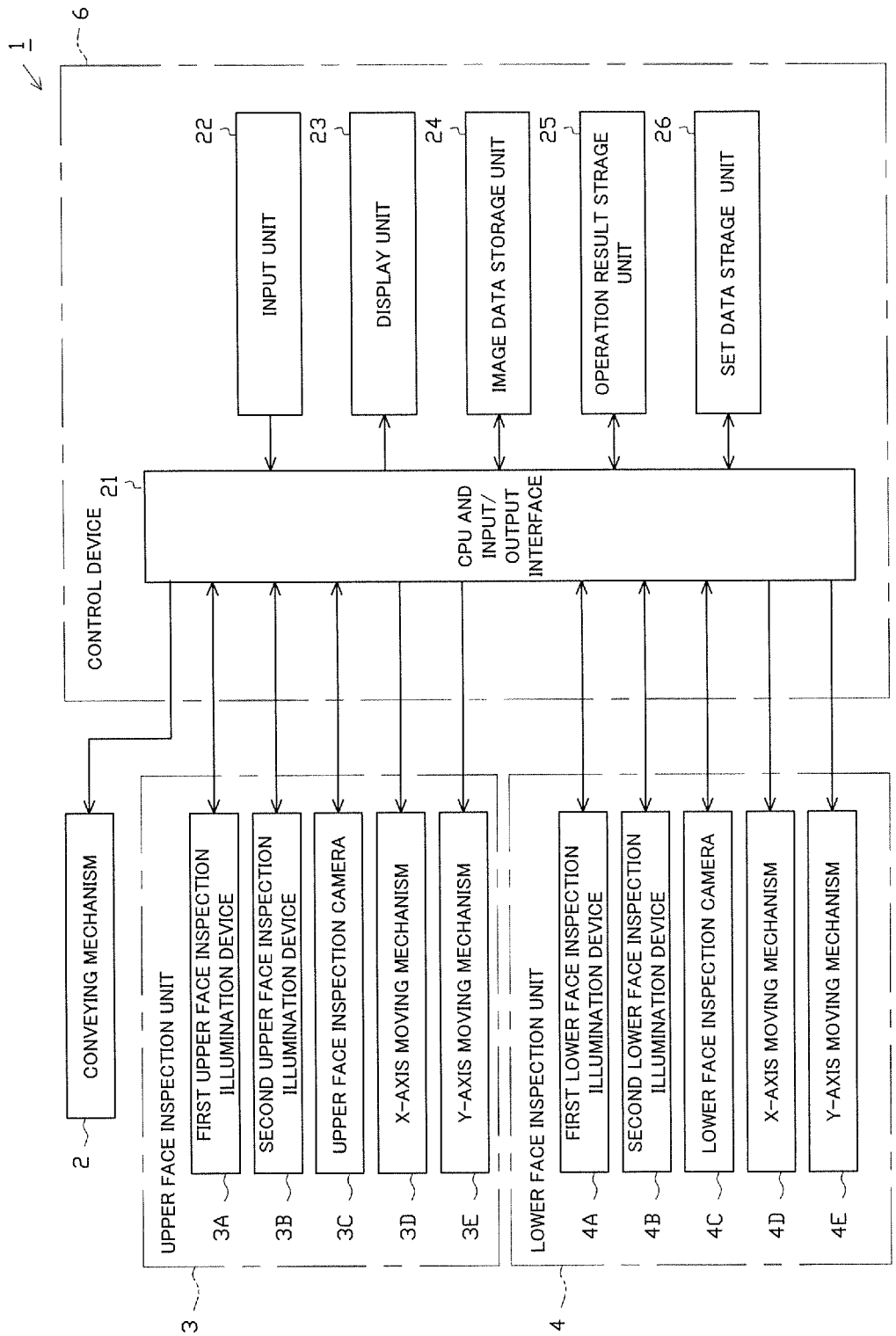
FIG. 3 is a block diagram illustrating the electrical configuration of the board inspection apparatus according to one or more embodiments of the invention.

The following describes the electrical configuration of the control device 6 with reference to FIG. 3. As shown in FIG. 3, the control device 6 includes a central processing unit (CPU) and input/output interface 21 configured to control the entire board inspection apparatus 1 (hereinafter referred to as "CPU and the like 21" or "processor"), an input unit 22 configured by, for example, a keyboard, a mouse and a touch panel and provided as "input means" or "input device," a display unit 23 configured to have a display screen such as a cathode ray tube (CRT) or liquid crystal screen and provided as "display means" or "display," an image data storage unit 24 configured to store image data and the like taken by the upper face inspection camera 3C and the lower face inspection camera 4C, an operation result storage unit 25 configured to store the results of various arithmetic operations, and a set data storage unit 26 configured to store in advance various information such as Gerber data. These respective units 22 to 26 are electrically connected with the CPU and the like 21.

The following describes an inspection routine performed by the board inspection apparatus 1 with regard to each of inspection areas on the upper face and on the lower face of the printed circuit board P1. This inspection routine is performed by the control device 6 (by the CPU and the like 21).

According to this embodiment, an image acquisition process is performed for inspection with regard to each of the inspection areas on the upper face side of the printed circuit board P1. The image acquisition process changes the phase of a stripe pattern that is emitted from the first upper face inspection illumination device 3A and performs four imaging processes with this stripe pattern of different phases. The image acquisition process subsequently changes the phase of a stripe pattern that is emitted from the second upper face inspection illumination device 3B and performs four imaging processes with this stripe pattern of different phases. The image acquisition process accordingly obtains a total of eight different image data (as shown by an upper part of FIG. 4).

Similarly, an image acquisition process is performed for inspection with regard to each of the inspection areas on the lower face side of the printed circuit board P1. The image acquisition process changes the phase of a stripe pattern that is emitted from the first lower face inspection illumination device 4A and performs four imaging processes with this stripe pattern of different phases. The image acquisition process subsequently changes the phase of a stripe pattern that is emitted from the second lower face inspection illumination device 4B and performs four imaging processes with this stripe pattern of different phases. The image acquisition process accordingly obtains a total of eight different image data (as shown by a lower part of FIG. 4).

Figure 4:
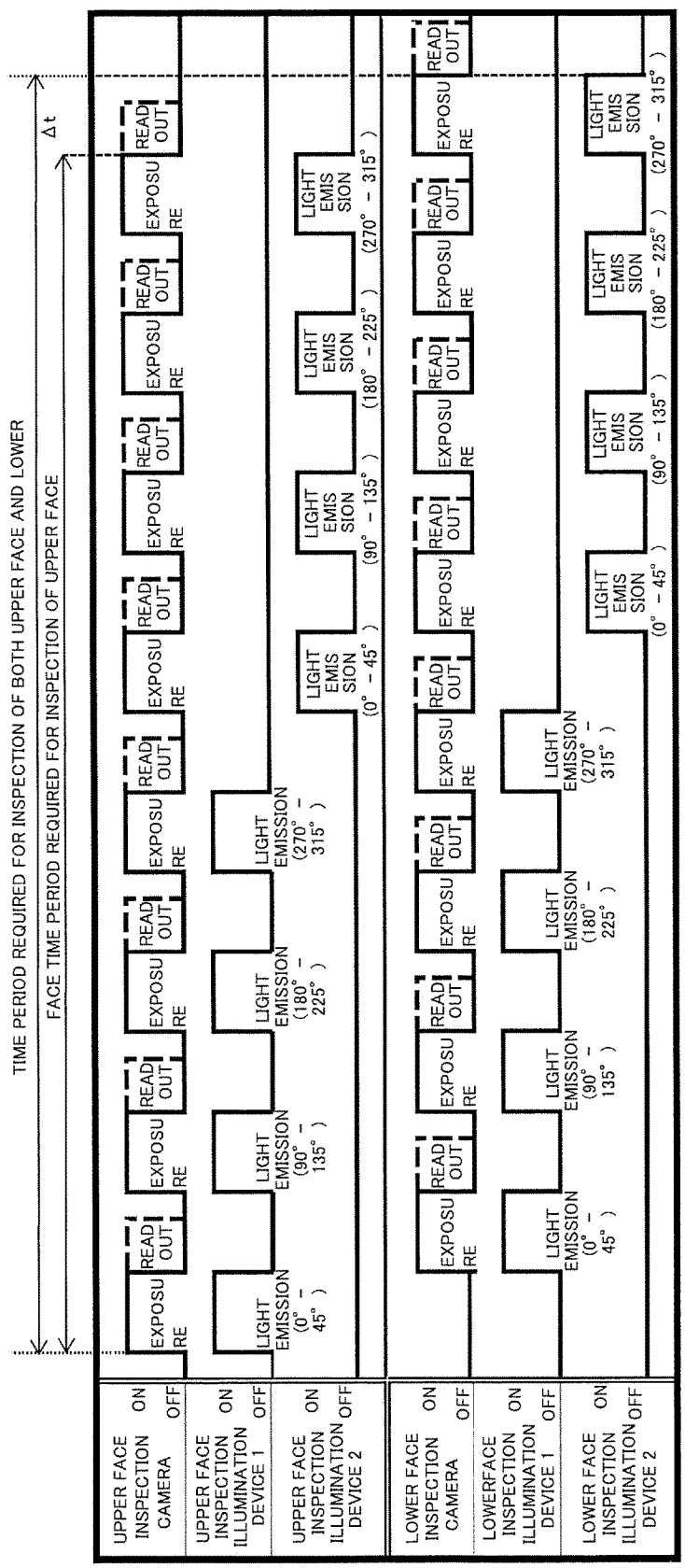
FIG. 4 is a timing chart illustrating processing operations of an upper face inspection unit and a lower face inspection unit in a specific process according to one or more embodiments of the invention.

FIG. 4 is a timing chart illustrating the processing operations of the upper face inspection unit 3 and the lower face inspection unit 4 in a specific process according to one or more embodiments of the invention, that is carried out when the processing period of the image acquisition process with regard to a predetermined inspection area on the upper face side of the printed circuit board P1 is at least partly overlapped with the processing period of the image acquisition process with regard to a predetermined inspection area on the lower face side of the printed circuit board P1 as described below.

The following describes the inspection routine performed with regard to each of the inspection areas in inspection on the upper face side of the printed circuit board P1 as an example.

The control device 6 first drives and controls the X-axis moving mechanism 3D and the Y-axis moving mechanism 3E so as to move the upper face inspection unit 3 and adjust the imaging view (imaging range) of the upper face inspection camera 3C to a predetermined inspection area on the upper face of the printed circuit board P1.

The control device 6 subsequently drives and controls the first upper face inspection illumination device 3A to set the position of the grid plate 3Ab to a default position (position at which the phase of the stripe pattern projected in a predetermined location is equal to "0 degree"). At the same time, the control device 6 drives and controls the second upper face inspection illumination device 3B to set the position of the grid plate 3Bb to a default position (position at which the phase of the stripe pattern projected in the predetermined location is equal to "0 degree").

After completion of such setting, the control device 6 drives and controls the first upper face inspection illumination device 3A and the upper face inspection camera 3C to start a first imaging process (exposure process) with a stripe pattern that is emitted from the first upper face inspection illumination device 3A.

For example, the control device 6 triggers light emission from the light source 3Aa of the first upper face inspection illumination device 3A so as to start emission of a stripe pattern and also starts the moving process of the grid plate 3Ab. This causes the stripe pattern projected in the inspection area to be continuously shifted at a constant speed along the Y-axis direction.

The control device 6 then starts an imaging process using the upper face inspection camera 3C, simultaneously with starting the emission of the stripe pattern (and starting the move of the grid plate 3Ab).

After the start of this first imaging process, the exposure is continued, while the phase of the stripe pattern projected in the predetermined location is changed from 0 degree to 45 degrees.

On termination of the first imaging process, the control device 6 stops the emission of light from the light source 3Aa and reads out image data taken by the upper face inspection camera 3C. The image data is then transferred from the upper face inspection camera 3C to the control device 6. The control device 6 stores the read-out image data into the image data storage unit 24.

The moving process of the grid plate 3Ab is, on the other hand, not terminated even after termination of the first imaging process, but is continued without any interruption until termination of a fourth imaging process with the stripe pattern that is emitted from the upper face inspection illumination device 3A.

Image data having a light intensity distribution in a sinusoidal wave form is obtained by continuously shifting the stripe pattern that is projected on the printed circuit board P1 and has the light intensity distribution in a square wave form or in a trapezoidal wave form and continuing imaging (exposure) of the stripe pattern (as described in JP 2015-231661A).

After elapse of a predetermined time period since termination of the first imaging process, at the timing when the phase of the stripe pattern that is to be projected in the predetermined location becomes equal to 90 degrees, the controller 6 again triggers light emission from the light source 3Aa of the first upper face inspection illumination device 3A so as to start emission of the stripe pattern and also starts an imaging process using the upper face inspection camera 3C. This starts a second imaging process with the stripe pattern that is emitted from the first upper face inspection illumination device 3A.

After the start of this second imaging process, the exposure is continued, while the phase of the stripe pattern projected in the predetermined location is changed from 90 degrees to 135 degrees.

On termination of the second imaging process, the control device 6 stops the emission of light from the light source 3Aa, reads out image data taken by the upper face inspection camera 3C, and stores the read-out image data into the image data storage unit 24.

After elapse of a predetermined time period since termination of the second imaging process, at the timing when the phase of the stripe pattern that is to be projected in the predetermined location becomes equal to 180 degrees, the controller 6 again triggers light emission from the light source 3Aa of the first upper face inspection illumination device 3A so as to start emission of the stripe pattern and also starts an imaging process using the upper face inspection camera 3C. This starts a third imaging process with the stripe pattern that is emitted from the first upper face inspection illumination device 3A.

After the start of this third imaging process, the exposure is continued, while the phase of the stripe pattern projected in the predetermined location is changed from 180 degrees to 225 degrees.

On termination of the third imaging process, the control device 6 stops the emission of light from the light source 3Aa, reads out image data taken by the upper face inspection camera 3C, and stores the read-out image data into the image data storage unit 24.

After elapse of a predetermined time period since termination of the third imaging process, at the timing when the phase of the stripe pattern that is to be projected in the predetermined location becomes equal to 270 degrees, the controller 6 again triggers light emission from the light source 3Aa of the first upper face inspection illumination device 3A so as to start emission of the stripe pattern and also starts an imaging process using the upper face inspection camera 3C. This starts a fourth imaging process with the stripe pattern that is emitted from the first upper face inspection illumination device 3A.

After the start of this fourth imaging process, the exposure is continued, while the phase of the stripe pattern projected in the predetermined location is changed from 270 degrees to 315 degrees.

On termination of the fourth imaging process, the control device 6 stops the emission of light from the light source 3Aa, reads out image data taken by the upper face inspection camera 3C, and stores the read-out image data into the image data storage unit 24. Additionally, the control device 6 terminates the moving process of the grid plate 3Ab.

After elapse of a predetermined time period since termination of the fourth imaging process (for example, after termination of a data transfer period), the control device 6 drives and controls the second upper face inspection illumination device 3B and the upper face inspection camera 3C to start a fifth imaging process with regard to the predetermined inspection area (i.e., a first imaging process with a stripe pattern that is emitted from the second upper face inspection illumination device 3B).

For example, the control device 6 triggers light emission from the light source 3Ba of the second upper face inspection illumination device 3B so as to start emission of a stripe pattern and also starts the moving process of the grid plate 3Bb. This causes the stripe pattern that is projected in the inspection area to be continuously shifted at a constant speed along the Y-axis direction.

The control device 6 then starts an imaging process using the upper face inspection camera 3C, simultaneously with starting the emission of the stripe pattern (and starting the move of the grid plate 3Bb).

After the start of this fifth imaging process, the exposure is continued, while the phase of the stripe pattern projected in the predetermined location is changed from 0 degree to 45 degrees.

On termination of the fifth imaging process, the control device 6 stops the emission of light from the light source 3Ba and reads out image data taken by the upper face inspection camera 3C. The image data is then transferred from the upper face inspection camera 3C to the control device 6. The control device 6 stores the read-out image data into the image data storage unit 24.

The moving process of the grid plate 3Bb is, on the other hand, not terminated even after termination of the fifth imaging process (i.e., the first imaging process with the stripe pattern that is emitted from the second upper face inspection illumination device 3B), but is continued without any interruption until termination of an eighth imaging process with regard to the predetermined inspection area (i.e., a fourth imaging process with the stripe pattern that is emitted from the second upper face inspection illumination device 3B).

After elapse of a predetermined time period since termination of the fifth imaging process, at the timing when the phase of the stripe pattern that is to be projected in the predetermined location becomes equal to 90 degrees, the controller 6 again triggers light emission from the light source 3Ba of the second upper face inspection illumination device 3B so as to start emission of the stripe pattern and also starts an imaging process using the upper face inspection camera 3C. This starts a sixth imaging process with regard to the predetermined inspection area (i.e., a second imaging process with the stripe pattern that is emitted from the second upper face inspection illumination device 3B).

After the start of this sixth imaging process, the exposure is continued, while the phase of the stripe pattern projected in the predetermined location is changed from 90 degrees to 135 degrees.

On termination of the sixth imaging process, the control device 6 stops the emission of light from the light source 3Ba, reads out image data taken by the upper face inspection camera 3C, and stores the read-out image data into the image data storage unit 24.

After elapse of a predetermined time period since termination of the sixth imaging process, at the timing when the phase of the stripe pattern that is to be projected in the predetermined location becomes equal to 180 degrees, the controller 6 again triggers light emission from the light source 3Ba of the second upper face inspection illumination device 3B so as to start emission of the stripe pattern and also starts an imaging process using the upper face inspection camera 3C. This starts a seventh imaging process with regard to the predetermined imaging area (i.e., a third imaging process with the stripe pattern that is emitted from the second upper face inspection illumination device 3B).

After the start of this seventh imaging process, the exposure is continued, while the phase of the stripe pattern projected in the predetermined location is changed from 180 degrees to 225 degrees.

On termination of the seventh imaging process, the control device 6 stops the emission of light from the light source 3Ba, reads out image data taken by the upper face inspection camera 3C, and stores the read-out image data into the image data storage unit 24.

After elapse of a predetermined time period since termination of the seventh imaging process, at the timing when the phase of the stripe pattern that is to be projected in the predetermined location becomes equal to 270 degrees, the controller 6 again triggers light emission from the light source 3Ba of the second upper face inspection illumination device 3B so as to start emission of the stripe pattern and also starts an imaging process using the upper face inspection camera 3C. This starts an eighth imaging process with regard to the predetermined inspection area (i.e., a fourth imaging process with the stripe pattern that is emitted from the second upper face inspection illumination device 3B).

After the start of this eighth imaging process, the exposure is continued, while the phase of the stripe pattern projected in the predetermined location is changed from 270 degrees to 315 degrees.

On termination of the eighth imaging process, the control device 6 stops the emission of light from the light source 3Ba, reads out image data taken by the upper face inspection camera 3C, and stores the read-out image data into the image data storage unit 24. Additionally, the control device 6 terminates the moving process of the grid plate 3Bb and then terminates the image acquisition process with regard to the predetermined inspection area.

Performing the image acquisition process (eight imaging processes) described above results in obtaining a total of eight different image data including four different image data taken with the stripe pattern that is emitted from the first upper face inspection illumination device 3A and four different image data taken with the stripe pattern that is emitted from the second upper face inspection illumination device 3B.

As described above, according to this embodiment, the four different image data taken with each of the stripe patterns are equivalent to four different image data taken by successively shifting the phase of a stripe pattern having a light intensity distribution in a sinusoidal wave form by 90 degrees each.

The control device 6 subsequently performs three-dimensional measurement (measurement of height) by a known phase shift method, based on the four different image data (luminance values of respective pixels) taken with each of the stripe patterns, and stores the result of this measurement into the operation result storage unit 25. According to this embodiment, the three-dimensional measurement is performed with emission of the stripe pattern from two different directions. This prevents the occurrence of any shaded area without emission of the stripe pattern.

The control device 6 subsequently performs a quality determination process of the solder paste P4, based on the result of the three-dimensional measurement (height data at each coordinate). For example, the control device 6 detects a printing range of the solder paste P4 that is higher than a reference plane, based on the result of the measurement with regard to the predetermined inspection area obtained as described above, and integrates the heights in respective locations in this printing range, so as to calculate the printed amount of the solder paste P4.

The control device 6 then compares the data obtained as described above with regard to the solder paste P4, for example, the location, the area and the height or the amount of the solder paste P4, with reference data (for example, Gerber data) stored in advance in the set data storage unit 26 and determines whether the printing state of the solder paste P4 is good or not with regard to the predetermined inspection area, based on whether the result of the comparison is within an allowable range.

After termination of the eighth imaging process described above, the control device 6 moves the upper face inspection unit 3 to a next inspection area, while performing the quality determination process described above. Repeating the series of processing described above with regard to all the inspection areas on the upper face of the printed circuit board P1 results in completing inspection of the entire upper face of the printed circuit board P1. The flow of inspection on the lower face side of the printed circuit board P1 is similar to the flow of inspection on the upper face side, so that its detailed description is omitted.

The following describes a specific process (processing operations of the upper face inspection unit 3 and the lower face inspection unit 4) that is carried out in the above configuration when the processing period of the image acquisition process with regard to a predetermined inspection area on the upper face side of the printed circuit board P1 is at least partly overlapped with the processing period of the image acquisition process with regard to a predetermined inspection area on the lower face side of the printed circuit board P1.

It is determined whether the processing period of the image acquisition process with regard to a predetermined inspection area on the upper face side of the printed circuit board P1 is at least partly overlapped with the processing period of the image acquisition process with regard to a predetermined inspection area on the lower face side of the printed circuit board P1, based on, for example, the Gerber data of the printed circuit board P1, prior to a start of inspection, for example, at the time when the printed circuit board P1 is carried into the board inspection apparatus 1.

According to one or more embodiments of the invention, the specific process described above alternately performs one imaging process using the upper face inspection camera 3C with regard to the upper face side of the printed circuit board P1 and one imaging process using the lower face inspection camera 4C with regard to the lower face side of the printed circuit board P1. This specific process is described in detail below with reference to FIG. 4.

As shown in FIG. 4, the control device 6 starts emission of a stripe pattern from the first upper face inspection illumination device 3A in the state that emission of a stripe pattern from the lower face inspection unit 4 (from the first lower face inspection illumination device 4A and the second lower face inspection illumination device 4B) is stopped, and starts a first imaging process using the upper face inspection camera 3C with regard to a predetermined inspection area on the upper face side of the printed circuit board P1 (i.e., a first imaging process with the stripe pattern that is emitted from the first upper face inspection illumination device 3A).

Simultaneously with termination of this imaging process with regard to the upper face side (corresponding to the phase of 0 degree to 45 degrees), the control device 6 stops emission of the stripe pattern from the first upper face inspection illumination device 3A, starts emission of a stripe pattern from the first lower face inspection illumination device 4A, and starts a first imaging process using the lower face inspection camera 4C with regard to a predetermined inspection area on the lower face side of the printed circuit board P1 (i.e., a first imaging process with the stripe pattern that is emitted from the first lower face inspection illumination device 4A).

Simultaneously with termination of this imaging process with regard to the lower face side (corresponding to the phase of 0 degree to 45 degrees), at the timing when a predetermined moving period of the grid plate 3Ab on the upper face side (corresponding to the phase of 45 degrees to 90 degrees) is terminated, the control device 6 stops emission of the stripe pattern from the first lower face inspection illumination device 4A, triggers light emission from the light source 3Aa so as to emit the stripe pattern from the first upper face inspection illumination device 3A, and starts a second imaging process using the upper face inspection camera 3C with regard to the predetermined inspection area on the upper face side of the printed circuit board P1 (i.e., a second imaging process with the stripe pattern that is emitted from the first upper face inspection illumination device 3A).

Simultaneously with termination of this imaging process with regard to the upper face side (corresponding to the phase of 90 degrees to 135 degrees), at the timing when a predetermined moving period of the grid plate 4Ab on the lower face side (corresponding to the phase of 45 degrees to 90 degrees) is terminated, the control device 6 stops emission of the stripe pattern from the first upper face inspection illumination device 3A, triggers light emission from the light source 4Aa so as to emit the stripe pattern from the first lower face inspection illumination device 4A, and starts a second imaging process using the lower face inspection camera 4C with regard to the predetermined inspection area on the lower face side of the printed circuit board P1 (i.e., a second imaging process with the stripe pattern that is emitted from the first lower face inspection illumination device 4A).

Simultaneously with termination of this imaging process with regard to the lower face side (corresponding to the phase of 90 degrees to 135 degrees), at the timing when a predetermined moving period of the grid plate 3Ab on the upper face side (corresponding to the phase of 135 degrees to 180 degrees) is terminated, the control device 6 stops emission of the stripe pattern from the first lower face inspection illumination device 4A, triggers light emission from the light source 3Aa so as to emit the stripe pattern from the first upper face inspection illumination device 3A, and starts a third imaging process using the upper face inspection camera 3C with regard to the predetermined inspection area on the upper face side of the printed circuit board P1 (i.e., a third imaging process with the stripe pattern that is emitted from the first upper face inspection illumination device 3A).

Simultaneously with termination of this imaging process with regard to the upper face side (corresponding to the phase of 180 degrees to 225 degrees), at the timing when a predetermined moving period of the grid plate 4Ab on the lower face side (corresponding to the phase of 135 degrees to 180 degrees) is terminated, the control device 6 stops emission of the stripe pattern from the first upper face inspection illumination device 3A, triggers light emission from the light source 4Aa so as to emit the stripe pattern from the first lower face inspection illumination device 4A, and starts a third imaging process using the lower face inspection camera 4C with regard to the predetermined inspection area on the lower face side of the printed circuit board P1 (i.e., a third imaging process with the stripe pattern that is emitted from the first lower face inspection illumination device 4A).

Simultaneously with termination of this imaging process with regard to the lower face side (corresponding to the phase of 180 degrees to 225 degrees), at the timing when a predetermined moving period of the grid plate 3Ab on the upper face side (corresponding to the phase of 225 degrees to 270 degrees) is terminated, the control device 6 stops emission of the stripe pattern from the first lower face inspection illumination device 4A, triggers light emission from the light source 3Aa so as to emit the stripe pattern from the first upper face inspection illumination device 3A, and starts a fourth imaging process using the upper face inspection camera 3C with regard to the predetermined inspection area on the upper face side of the printed circuit board P1 (i.e., a fourth imaging process with the stripe pattern that is emitted from the first upper face inspection illumination device 3A).

Simultaneously with termination of this imaging process with regard to the upper face side (corresponding to the phase of 270 degrees to 315 degrees), at the timing when a predetermined moving period of the grid plate 4Ab on the lower face side (corresponding to the phase of 225 degrees to 270 degrees) is terminated, the control device 6 stops emission of the stripe pattern from the first upper face inspection illumination device 3A, triggers light emission from the light source 4Aa so as to emit the stripe pattern from the first lower face inspection illumination device 4A, and starts a fourth imaging process using the lower face inspection camera 4C with regard to the predetermined inspection area on the lower face side of the printed circuit board P1 (i.e., a fourth imaging process with the stripe pattern that is emitted from the first lower face inspection illumination device 4A).

Simultaneously with termination of this imaging process with regard to the lower face side (corresponding to the phase of 270 degrees to 315 degrees), the control device 6 stops emission of the stripe pattern from the first lower face inspection illumination device 4A, triggers light emission from the light source 3Ba so as to emit a stripe pattern from the second upper face inspection illumination device 3B, and starts a fifth imaging process using the upper face inspection camera 3C with regard to the predetermined inspection area on the upper face side of the printed circuit board P1 (i.e., a first imaging process with the stripe pattern that is emitted from the second upper face inspection illumination device 3B).

Simultaneously with termination of this imaging process with regard to the upper face side (corresponding to the phase of 0 degree to 45 degrees), the control device 6 stops emission of the stripe pattern from the second upper face inspection illumination device 3B, triggers light emission from the light source 4Ba so as to emit a stripe pattern from the second lower face inspection illumination device 4B, and starts a fifth imaging process using the lower face inspection camera 4C with regard to the predetermined inspection area on the lower face side of the printed circuit board P1 (i.e., a first imaging process with the stripe pattern that is emitted from the second lower face inspection illumination device 4B).

Simultaneously with termination of this imaging process with regard to the lower face side (corresponding to the phase of 0 degree to 45 degrees), at the timing when a predetermined moving period of the grid plate 3Bb on the upper face side (corresponding to the phase of 45 degrees to 90 degrees) is terminated, the control device 6 stops emission of the stripe pattern from the second lower face inspection illumination device 4B, triggers light emission from the light source 3Ba so as to emit the stripe pattern from the second upper face inspection illumination device 3B, and starts a sixth imaging process using the upper face inspection camera 3C with regard to the predetermined inspection area on the upper face side of the printed circuit board P1 (i.e., a second imaging process with the stripe pattern that is emitted from the second upper face inspection illumination device 3B).

Simultaneously with termination of this imaging process with regard to the upper face side (corresponding to the phase of 90 degrees to 135 degrees), at the timing when a predetermined moving period of the grid plate 4Bb on the lower face side (corresponding to the phase of 45 degrees to 90 degrees) is terminated, the control device 6 stops emission of the stripe pattern from the second upper face inspection illumination device 3B, triggers light emission from the light source 4Ba so as to emit the stripe pattern from the second lower face inspection illumination device 4B, and starts a sixth imaging process using the lower face inspection camera 4C with regard to the predetermined inspection area on the lower face side of the printed circuit board P1 (i.e., a second imaging process with the stripe pattern that is emitted from the second lower face inspection illumination device 4B).

Simultaneously with termination of this imaging process with regard to the lower face side (corresponding to the phase of 90 degrees to 135 degrees), at the timing when a predetermined moving period of the grid plate 3Bb on the upper face side (corresponding to the phase of 135 degrees to 180 degrees) is terminated, the control device 6 stops emission of the stripe pattern from the second lower face inspection illumination device 4B, triggers light emission from the light source 3Ba so as to emit the stripe pattern from the second upper face inspection illumination device 3B, and starts a seventh imaging process using the upper face inspection camera 3C with regard to the predetermined inspection area on the upper face side of the printed circuit board P1 (i.e., a third imaging process with the stripe pattern that is emitted from the second upper face inspection illumination device 3B).

Simultaneously with termination of this imaging process with regard to the upper face side (corresponding to the phase of 180 degrees to 225 degrees), at the timing when a predetermined moving period of the grid plate 4Bb on the lower face side (corresponding to the phase of 135 degrees to 180 degrees) is terminated, the control device 6 stops emission of the stripe pattern from the second upper face inspection illumination device 3B, triggers light emission from the light source 4Ba so as to emit the stripe pattern from the second lower face inspection illumination device 4B, and starts a seventh imaging process using the lower face inspection camera 4C with regard to the predetermined inspection area on the lower face side of the printed circuit board P1 (i.e., a third imaging process with the stripe pattern that is emitted from the second lower face inspection illumination device 4B).

Simultaneously with termination of this imaging process with regard to the lower face side (corresponding to the phase of 180 degrees to 225 degrees), at the timing when a predetermined moving period of the grid plate 3Bb on the upper face side (corresponding to the phase of 225 degrees to 270 degrees) is terminated, the control device 6 stops emission of the stripe pattern from the second lower face inspection illumination device 4B, triggers light emission from the light source 3Ba so as to emit the stripe pattern from the second upper face inspection illumination device 3B, and starts an eighth imaging process using the upper face inspection camera 3C with regard to the predetermined inspection area on the upper face side of the printed circuit board P1 (i.e., a fourth imaging process with the stripe pattern that is emitted from the second upper face inspection illumination device 3B).

Simultaneously with termination of this imaging process with regard to the upper face side (corresponding to the phase of 270 degrees to 315 degrees), at the timing when a predetermined moving period of the grid plate 4Bb on the lower face side (corresponding to the phase of 225 degrees to 270 degrees) is terminated, the control device 6 stops emission of the stripe pattern from the second upper face inspection illumination device 3B, triggers light emission from the light source 4Ba so as to emit the stripe pattern from the second lower face inspection illumination device 4B, and performs an eighth imaging process using the lower face inspection camera 4C with regard to the predetermined inspection area on the lower face side of the printed circuit board P1 (i.e., a fourth imaging process with the stripe pattern that is emitted from the second lower face inspection illumination device 4B (corresponding to the phase of 270 degrees to 315 degrees)).

At the stage when the eighth imaging process using the upper face inspection camera 3C with regard to the predetermined inspection area on the upper face side of the printed circuit board P1 is terminated, the upper face inspection unit 3 is moved to a next inspection area. At the stage when the eighth imaging process using the lower face inspection camera 4C with regard to the predetermined inspection area on the lower face side of the printed circuit board P1 is terminated, the lower face inspection unit 4 is moved to a next inspection area.

As described above in detail, the configuration of this embodiment stops emission of the stripe pattern on the lower face side (or on the upper face side) during an imaging period with regard to the upper face side (or with regard to the lower face side) of the printed circuit board P1, in the specific process that is carried out when the processing period of the image acquisition process with regard to a predetermined inspection area on the upper face side of the printed circuit board P1 is at least partly overlapped with the processing period of the image acquisition process with regard to a predetermined inspection area on the lower face side of the printed circuit board P1. This configuration enables image data of the high accuracy to be obtained without causing leakage of light to the upper face side (or to the lower face side). As a result, this improves the inspection accuracy with regard to double-sided inspection of the printed circuit board P1.

Additionally, the above specific process is configured to perform an imaging process with regard to the upper face side (or with regard to the lower face side) of the printed circuit board P1 and subsequently perform an imaging process with regard to the lower face side (or with regard to the upper face side) of the printed circuit board P1. Accordingly, alternately repeating the imaging process with regard to the upper face side of the printed circuit board P1 and the imaging process with regard to the lower face side of the printed circuit board P1 enables the image acquisition process (a plurality of imaging processes) with regard to a predetermined inspection area on the upper face side of the printed circuit board P1 and the image acquisition process (a plurality of imaging processes) with regard to a predetermined inspection area on the lower face side of the printed circuit board P1 to be performed at the same time.

According to this embodiment, as shown in FIG. 4, an image acquisition process with regard to both the upper face and the lower face of the printed circuit board P1 can be completed by adding only a time period $\Delta t$ required for only one imaging process with regard to the lower face side of the printed circuit board P1 to a time period required for the image acquisition process (a plurality of imaging processes) with regard to a predetermined inspection area on the upper face side of the printed circuit board P1.

Accordingly, this configuration increases the inspection speed for double-sided inspection of the printed circuit board P1, compared with, for example, a configuration that performs the image acquisition process (a plurality of imaging processes) with regard to a predetermined inspection area on the lower face side of the printed circuit board P1 after completion of the image acquisition process (a plurality of imaging processes) with regard to a predetermined inspection area on the upper face side of the printed circuit board P1.

As a result, this improves the inspection accuracy with regard to double-sided inspection of the printed circuit board P1 and increases the speed of the inspection.

The present disclosure is not limited to the description of the above embodiments but may be implemented, for example, by aspects described below. The following description is, however, also only illustrative and the present disclosure may naturally be implemented by any other applications and modifications.

(a) According to the above embodiments, the board inspection apparatus is implemented as the solder printing inspection apparatus configured to perform an inspection for the printing state of the solder paste P4 printed on the printed circuit board P1. The board inspection apparatus is, however, not limited to this configuration but may be configured to perform an inspection for another object, for example, a solder bump printed on a board or an electronic component mounted on a board. The board inspection apparatus is also not limitedly used for inspection prior to reflow but may be used for inspection after reflow.

(b) The above embodiments are configured to obtain four different image data with a stripe pattern of different phases shifted by 90 degrees each for three-dimensional measurement by the phase shift method. The number of phase shifts and the amount of each phase shift are, however, not limited to those of this embodiment. Any other allowable number of phase shifts and any other allowable amount of each phase shift may be employed for three-dimensional measurement by the phase shift method.

For example, one modified configuration may obtain three different image data having different phases shifted by 120 degrees each (or by 90 degrees each) for three-dimensional measurement. Another modified configuration may obtain two different image data having different phases shifted by 180 degrees each (or by 90 degrees each) for three-dimensional measurement.

(c) The above embodiments are configured to continuously shift the stripe pattern that is projected on the printed circuit board P1 and has a light intensity distribution in a square wave form or in a trapezoidal wave form and continue imaging (exposure) of the stripe pattern, so as to obtain image data having a light intensity distribution in a sinusoidal wave form.

The imaging period in which imaging is to be continued is not limited to the time period of the above embodiments (corresponding to the move by the phase of 45 degrees), but a different configuration may be employed for this imaging period.

The configuration that continues imaging (exposure) is not essential. Like the prior art, one modified configuration may successively change the position of a grid and emit a stripe pattern in the state that the grid is at stop, so as to obtain a plurality of image data having different phases.

According to the above embodiments, the grid plate is employed as the means for converting light emitted from a light source into a stripe pattern. This is, however, not restrictive, and any other suitable means, for example, a liquid crystal panel configured to control the transmittance or the reflectance with respect to each reed-shaped line, may be employed. Using such a liquid crystal panel or the like allows for emission of a stripe pattern having a light intensity distribution in an ideal sinusoidal wave form without continuously moving a grid plate.

(d) The above embodiments are configured to perform three-dimensional measurement by the phase shift method. The phase shift method is, however, not essential but another three-dimensional measurement method, for example, a space code method, may be employed. It is, however, more preferable to employ a measurement method of the high measurement accuracy, for example, the phase shift method, for measurement of a small measurement object such as the solder paste P4.

(e) The configuration involved in the irradiator, for example, the type of light emitted from each illumination device, is not limited to the configuration of the above embodiments, but another configuration may be employed.

For example, the above embodiments are configured to emit a stripe pattern and perform three-dimensional measurement for inspection of the printed circuit board P1. One modified configuration may perform two-dimensional measurement, in place of or in addition to the configuration of the embodiments.

Figure 5:
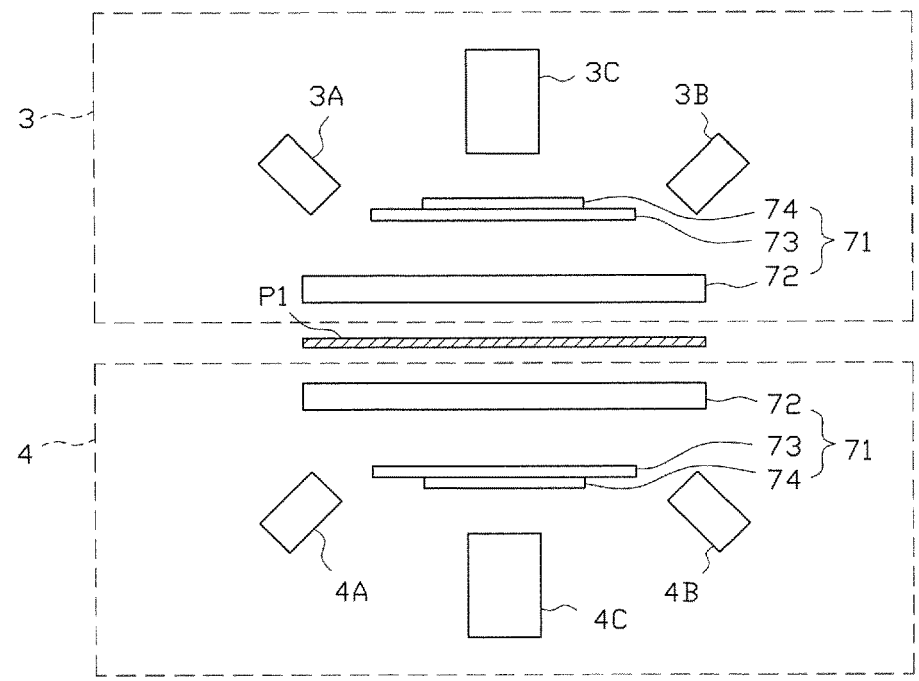
FIG. 5 is a schematic configuration diagram schematically illustrating a board inspection apparatus according to one or more embodiments of the invention.

For example, as shown in FIG. 5, the upper face inspection unit 3 may be configured to include an illumination device 71 for two-dimensional inspection, in addition to the first upper face inspection illumination device 3A, the second upper face inspection illumination device 3B and the upper face inspection camera 3C. The lower face inspection unit 4 may also be configured to include an illumination device 71 for two-dimensional measurement, in addition to the first lower face inspection illumination device 4A, the second lower face inspection illumination device 4B and the lower face inspection camera 4C.

Figure 6:
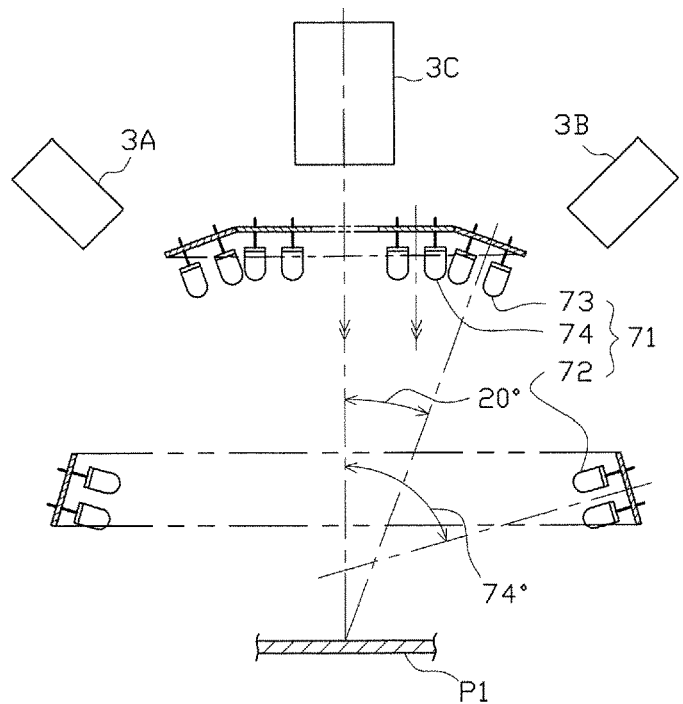
FIG. 6 is a partly enlarged sectional view illustrating an illumination device for two-dimensional inspection according to one or more embodiments of the invention.

As shown in FIGS. 5 and 6, the illumination device 71 includes a first ring light 72 located closest to the printed circuit board P1, a second ring light 73 located second closest to the printed circuit board P1 next to the first ring light 72 and a third ring light 74 located at a position most away from the printed circuit board P1.

Each of the ring lights 72 to 74 is configured to switch over emission of three monochromatic lights, i.e., red light, green light and blue light. The first ring light 72 is configured to irradiate the printed circuit board P1 with light at a large incident angle (for example, 74 degrees). The second ring light 73 is configured to irradiate the printed circuit board P1 with light at an intermediate incident angle (for example, 20 degrees). The third ring light 74 is configured to irradiate the printed circuit board P1 with light at a small incident angle (for example, 0 degree).

One modified configuration employed for inspection (image acquisition process), for example, with regard to a predetermined inspection area on the upper face side of the printed circuit board P1 may perform at least one imaging process among one imaging process with the red light emitted from all the ring lights 72 to 74, one imaging process with the blue light emitted from all the ring lights 72 to 74, one imaging process with the green light emitted from all the ring lights 72 to 74, one imaging process with the monochromatic light (for example, blue light) emitted from the first ring light 72 at a large incident angle, one imaging process with the monochromatic light (for example, green light) emitted from the second ring light 73 at an intermediate incident angle and one imaging process with the monochromatic light (for example, red light) emitted from the third ring light 74 at a small incident angle, in addition to at least either one of a plurality of imaging processes with a stripe pattern emitted from the first upper face inspection illumination device 3A and a plurality of imaging processes with a stripe pattern emitted from the second upper face inspection illumination device 3B (the same applies to inspection on the lower face side of the printed circuit board P1).

The above configuration may be modified to perform any of various two-dimensional measurements, for example, extraction of any of various areas such as solder printing area, electrode area and silk printing area, detection of any foreign substance, measurement of the area of the solder paste P4, detection of a positional misalignment or bridge detection, in addition to the three-dimensional measurement.

A specific process similar to that of the above embodiments is also carried out in this modified configuration when the processing period of the image acquisition process with regard to a predetermined inspection area on the upper face side of the printed circuit board P1 is at least partly overlapped with the processing period of the image acquisition process with regard to a predetermined inspection area on the lower face side of the printed circuit board P1. This specific process alternately performs one imaging process using the upper face inspection camera 3C with regard to the upper face side of the printed circuit board P1 and one imaging process using the lower face inspection camera 4C with regard to the lower face side of the printed circuit board P1.

One example of this modified configuration may sequentially perform one imaging process with regard to the upper face side of the printed circuit board P1 with the red light emitted from all the ring lights 72 to 74, one imaging process with regard to the lower face side of the printed circuit board P1 with the red light emitted from all the ring lights 72 to 74, one imaging process with regard to the upper face side of the printed circuit board P1 with the monochromatic light (for example, blue light) emitted from the first ring light 72 at a large incident angle and one imaging process with regard to the lower face side of the printed circuit board P1 with the monochromatic light (for example, blue light) emitted from the first ring light 72 at a large incident angle.

Another modified configuration may not perform the three-dimensional measurement but perform only two-dimensional measurement with omission of the first upper face inspection illumination device 3A, the second upper face inspection illumination device 3B, the first lower face inspection illumination device 4A and the second lower face inspection illumination device 4B.

(f) The above embodiments are configured to independently drive and control the upper face inspection unit 3 and the lower face inspection unit 4 and is configured to carry out the specific process only when the processing period of the image acquisition process with regard to a predetermined inspection area on the upper face side of the printed circuit board P1 is at least partly overlapped with the processing period of the image acquisition process with regard to a predetermined inspection area on the lower face side of the printed circuit board P1. This configuration is, however, not essential, but another configuration may be employed.

For example, one modified configuration may drive and control the upper face inspection unit 3 and the lower face inspection unit 4 in synchronism with each other and consistently carry out the specific process described above.

Another modified configuration may continuously convey the printed circuit board P1 while fixing the upper face inspection unit 3 and the lower face inspection unit 4 and may perform an inspection with regard to both the upper face and the lower face of the printed circuit board P1 with consistently carrying out the specific process described above.

(g) The processing operations of the upper face inspection unit 3 and the lower face inspection unit 4 in the specific process are not limited to the processing operations in the above embodiments (i.e., the example shown in FIG. 4). Any other configuration may be employed as long as the configuration stops emission of light on the lower face side (or on the upper face side) at least during an imaging period with regard to the upper face side (or with regard to the lower face side) of the printed circuit board P1 and thereby prevents leakage of light to the upper face side (or to the lower face side).

For example, according to the above embodiments, the data transfer (read-out) period of each inspection camera 3C or 4C is set to be shorter than the processing period of one imaging process using each inspection camera 3C or 4C. One modified configuration may set the data transfer period to be longer than the processing period of one imaging process.

For example, this modified configuration may start data transfer by the upper face inspection camera 3C after termination of an imaging process using the upper face inspection camera 3C, and concurrently start an imaging process using the lower face inspection camera 4C. After termination of this imaging process using the lower face inspection camera 4C, the modified configuration may wait for termination of a data transfer period by the upper face inspection camera 3C (i.e., a time period in which an imaging process is not allowed to be performed) and start a next imaging process using the upper face inspection camera 3C. Another modified configuration may start data transfer by the upper face inspection camera 3C after termination of an imaging process using the upper face inspection camera 3C, and start an imaging process using the lower face inspection camera 4C after elapse of a predetermined time period (for example, 1 msec).

In any of these modified configurations, the operating and control processes of the respective grid plates such as the grid plate 3Ab are naturally performed according to the imaging processes using the respective inspection cameras 3C and 4C. In other words, the grid plate should be stopped to stand by when there is a time lag.

(g) According to the above embodiments, a CCD sensor is employed as the imaging element of each of the inspection cameras 3C and 4C. This imaging element is, however, not essential, but another imaging element such as CMOS sensor may be employed.

A configuration using a conventional CCD sensor or the like is not allowed to perform a next imaging (exposure) process during data transfer. Accordingly the imaging process and the data transfer process are to be alternately repeated when a plurality of imaging processes are required.

A configuration using a CMOS sensor or a CCD sensor having the function of allowing for exposure during data transfer, on the other hand, allows the imaging process and the data transfer process to be performed in a partly overlapped manner.

When the data transfer period is set longer than the processing period of one imaging process as described above, for example, the latter configuration may start data transfer by the upper face inspection camera 3C after termination of an imaging process using the upper face inspection camera 3C, and concurrently start an imaging process using the lower face inspection camera 4C. Without waiting for termination of a data transfer period by the upper face inspection camera 3C, this configuration may start a next imaging process using the upper face inspection camera 3C, simultaneously with termination of the imaging process using the lower face inspection camera 4C.

Figure 7:
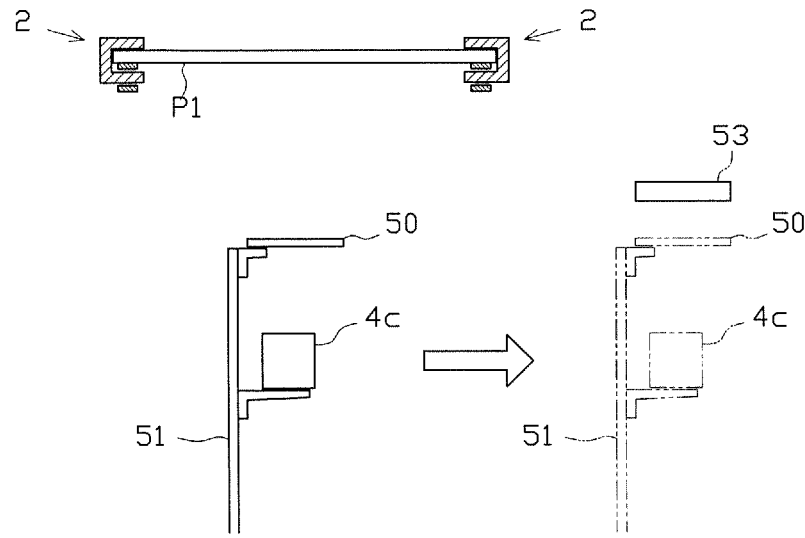
FIG. 7 is a schematic configuration diagram schematically illustrating one example of a protective cover for a lower face inspection camera and its inspection mechanism according to one or more embodiments of the invention.

(h) Although not being specifically referred to in the above embodiments, for example, the lower face inspection camera 4C located below the conveying path of the printed circuit board P1 may be provided with a protective cover 50 as shown in FIG. 7.

There is a possibility that a foreign substance such as solder residue falling down from the printed circuit board P1 may adhere to the lower face inspection camera 4C located below the conveying path of the printed circuit board P1. Providing the protective cover 50 suppresses any foreign substance from adhering to the lower face inspection camera 4C.

The protective cover 50 is formed from a transparent member, and the lower inspection camera 4C is allowed to take an image of the lower face of the printed circuit board P1 across the protective cover 50.

Deposition of any dirt or adhesion of any foreign substance on the protective cover 50 is, however, likely to interfere with the inspection. Accordingly, the board inspection apparatus 1 may comprise a cover inspection mechanism configured to perform an inspection in order to determine whether any foreign substance or the like adheres to the protective cover 50. The following describes a concrete example of the cover inspection mechanism.

As shown in FIG. 7, the lower face inspection camera 4C and the protective cover 50 are integrally assembled by means of a holder 51. The lower face inspection camera 4C and the protective cover 50 together with the holder 51 are moved to a position that deviates from the position below the conveying path of the printed circuit board P1 (cover inspection position) by non-illustrated drive means during a time period after a printed circuit board P1 for which inspection has been just completed is carried out of the board inspection apparatus 1 and before a new printed circuit board P1 is carried into the board inspection apparatus 1.

A transmitted illumination device 53 is provided at the cover inspection position to be located above the protective cover 50. After the camera 4C is focused on the protective cover 50, the camera 4C serves to take an image of the transmitted light that is emitted from the transmitted illumination device 53 and is transmitted through the protective cover 50, for the purpose of inspection of foreign substance.

Figure 8:
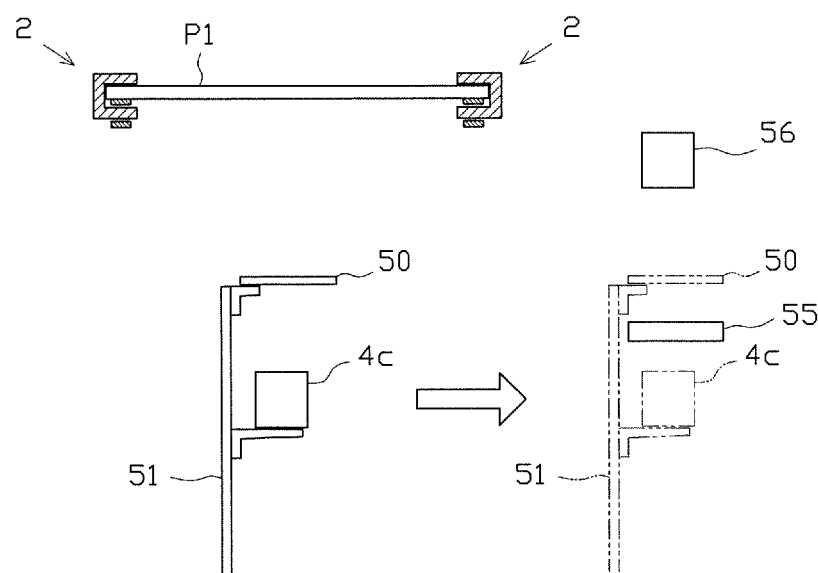
FIG. 8 is a schematic configuration diagram schematically illustrating another example of the protective cover for the lower face inspection camera and its inspection mechanism according to one or more embodiments of the invention.

Like an example shown in FIG. 8, a transmitted illumination device 55 placed below the protective cover 50 may be provided at the cover inspection position, and a camera 56 exclusively used for inspection of the cover may be provided at a position above the protective cover 50. The camera 56 serves to take an image of the transmitted light that is emitted from the transmitted illumination device 55 and is transmitted through the protective cover 50, for the purpose of inspection of foreign substance.

Figure 9:
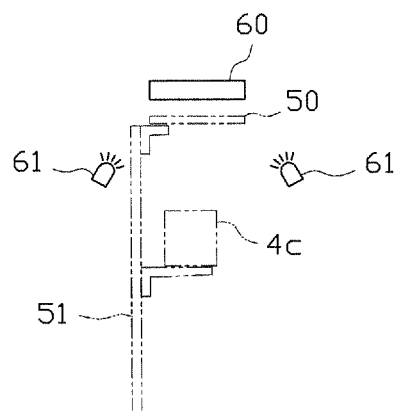
FIG. 9 is a schematic configuration diagram schematically illustrating another example of the protective cover for the lower face inspection camera and its inspection mechanism according to one or more embodiments of the invention.

A reflected illumination device may be used, in place of the transmitted illumination device, for inspection of foreign substance. For example, as shown in FIG. 9, a blackboard 60 may be provided at the cover inspection position to be located above the protective cover 50, and a reflected illumination device 61 may be provided to irradiate the protective cover 50 with light emitted obliquely upward. After the camera 4C is focused on the protective cover 50, the camera 4C serves to take an image of the reflected light that is emitted from the reflected illumination device 61 and is reflected from the protective cover 50, for the purpose of inspection of foreign substance.

Figure 10:
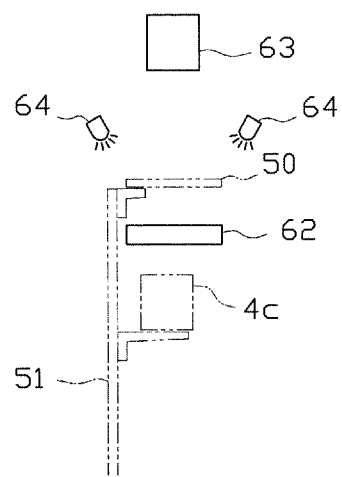
FIG. 10 is a schematic configuration diagram schematically illustrating another example of the protective cover for the lower face inspection camera and its inspection mechanism according to one or more embodiments of the invention.

Like an example shown in FIG. 10, a blackboard 62 placed below the protective cover 50, a camera 63 located above the protective cover 50 and exclusively used for inspection of the cover, and a reflected illumination device 64 configured to irradiate the protective cover 50 with light emitted obliquely downward may be provided at the cover inspection position. The camera 63 serves to take an image of the reflected light that is emitted from the reflected illumination device 64 and is reflected from the protective cover 50, for the purpose of inspection of foreign substance.

A mechanism configured to remove the foreign substance from the protective cover 50 may be provided in addition to any of the various cover inspection mechanisms described above. When any foreign substance or the like is detected on the protective cover 50 by any of the various cover inspection mechanisms described above, a predetermined foreign substance removal mechanism may be activated to remove the foreign substance.

Examples of the foreign substance removal mechanism include a mechanism configured to spray the air and thereby blow out any foreign substance from the protective cover 50, a mechanism configured to sweep away any foreign substance by means of a brush or the like, a mechanism configured to place thin films on the protective cover 50 and successively peel off a stained thin film (tear off function), and a mechanism configured to place a film roll on the protective cover 50 and successively roll up a stained part of the film roll (roll off function).

A protective cover configured to protect the entire lower face inspection unit 4 may be provided, in place of the protective cover 50 configured to protect only the lower face inspection camera 4C. The protective cover configured to protect the entire lower face inspection unit 4 is, however, likely to provide a side inspection area in the inspection of foreign substance and increase the inspection time. This modified configuration also increases the size of the protective cover and is thereby likely to expand the size of the entire apparatus and increase the overall weight of the apparatus. From these points of view, it is more preferable to provide the protective cover 50 configured to protect only the lower face inspection camera 4C.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST 1 board inspection apparatus, 2 conveying mechanism, 3 upper face inspection unit, 3A first upper face inspection illumination device, 3B second upper face inspection illumination device, 3C upper face inspection camera, 4 lower face inspection unit, 4A first lower face inspection illumination device, 4B second lower face inspection illumination device, 4C lower face inspection camera, 6 control device, P1 printed circuit board, P4 solder paste

What is claim is:

1. A board inspection apparatus comprising:
   a surface-side irradiator that irradiates a first predetermined inspection area on a surface side of a board with first predetermined light;
   a surface-side camera that takes an image of the first predetermined inspection area irradiated with the first predetermined light;
   a rear face-side irradiator that irradiates a second predetermined inspection area on a rear face side of the board with second predetermined light;
   a rear face-side camera that takes an image of the second predetermined inspection area irradiated with the second predetermined light; and a controller that inspects
the first predetermined inspection area based on a plurality of image data obtained from the surface-side camera, and
the second predetermined inspection area based on a plurality of image data obtained from the rear face-side camera, wherein
the controller alternately executes each of a first plurality of imaging processes by the surface-side camera and each of a second plurality of imaging processes by the rear face-side camera by:
starting emission of the first predetermined light and stopping emission of the second predetermined light to execute one of the first plurality of imaging processes, and subsequently stopping emission of the first predetermined light and starting emission of the second predetermined light to execute one of the second plurality of imaging processes, or
starting emission of the second predetermined light and stopping emission of the first predetermined light to execute one of the second plurality of imaging processes, and subsequently stopping emission of the second predetermined light and starting emission of the first predetermined light to execute one of the first plurality of imaging processes,
each of the first predetermined light and the second predetermined light is patterned light having a light intensity distribution of a stripe shape, and
a first time period during which the each of the first plurality of imaging processes is executed and a second time period during which the each of the second plurality of imaging processes is executed are repeated alternately, wherein the first time period and the second time period each correspond to a predetermined phase of the patterned light.

2. The board inspection apparatus according to claim 1, wherein the surface-side camera is prohibited from executing the each of the first plurality of imaging processes during the second time period, and
the rear face-side camera is prohibited from executing the each of the second plurality of imaging processes during the first time period.

3. The board inspection apparatus according to claim 1, wherein the surface-side irradiator and the surface-side camera are driven and controlled independently of the rear face-side irradiator and the rear face-side camera,
the plurality of image data from the surface-side camera and the plurality of image data from the rear face-side camera are obtained independently, and
the controller alternately executes the imaging processes when a period for obtaining the plurality of image data from the surface-side camera is at least partly overlapped with a period for obtaining the plurality of image data from the rear face-side camera.

4. The board inspection apparatus according to claim 2, wherein the surface-side irradiator and the surface-side camera are driven and controlled independently of the rear face-side irradiator and the rear face-side camera,
the plurality of image data from the surface-side camera and the plurality of image data from the rear face-side camera are obtained independently, and
the controller alternately executes the imaging processes when a period for obtaining the plurality of image data from the surface-side camera is at least partly overlapped with a period for obtaining the plurality of image data from the rear face-side camera.

5. The board inspection apparatus according to claim 1, the controller executes three-dimensional measurement by a phase shift method, based on a plurality of image data taken with the patterned light of different phases.

6. The board inspection apparatus according to claim 2, the controller executes three-dimensional measurement by a phase shift method, based on a plurality of image data taken with the patterned light of different phases.

7. The board inspection apparatus according to claim 3, the controller executes three-dimensional measurement by a phase shift method, based on a plurality of image data taken with the patterned light of different phases.

8. The board inspection apparatus according to claim 4, the controller executes three-dimensional measurement by a phase shift method, based on a plurality of image data taken with the patterned light of different phases.

9. The board inspection apparatus according to claim 1, wherein the board is either a printed circuit board on which solder paste is printed or a wafer substrate on which a solder bump is formed.

10. The board inspection apparatus according to claim 2, wherein the board is either a printed circuit board on which solder paste is printed or a wafer substrate on which a solder bump is formed.

11. The board inspection apparatus according to claim 3, wherein the board is either a printed circuit board on which solder paste is printed or a wafer substrate on which a solder bump is formed.

12. The board inspection apparatus according to claim 4, wherein the board is either a printed circuit board on which solder paste is printed or a wafer substrate on which a solder bump is formed.

13. The board inspection apparatus according to claim 5, wherein the board is either a printed circuit board on which solder paste is printed or a wafer substrate on which a solder bump is formed.

14. The board inspection apparatus according to claim 6, wherein the board is either a printed circuit board on which solder paste is printed or a wafer substrate on which a solder bump is formed.

15. The board inspection apparatus according to claim 7, wherein the board is either a printed circuit board on which solder paste is printed or a wafer substrate on which a solder bump is formed.

16. The board inspection apparatus according to claim 8, wherein the board is either a printed circuit board on which solder paste is printed or a wafer substrate on which a solder bump is formed.

17. The board inspection apparatus according to claim 1, wherein the predetermined phase of the patterned light is 45 degrees.

18. The board inspection apparatus according to claim 1, wherein
the controller:
reads out image data obtained by the each of the first plurality of imaging processes, within the second time period, and
reads out image data obtained by the each of the second plurality of imaging processes, within the first time period.

19. A board inspection apparatus comprising:
a surface-side irradiator that emits first light to a first inspection area on a surface side of a board;
a surface-side camera that takes a first plurality of images of the first inspection area;
a rear face-side irradiator that emits second light to a second inspection area on a rear face side of the board;

a rear face-side camera that takes a second plurality of images of the second inspection area; and a controller that causes the surface-side camera and the rear face-side camera to alternately take each of the first and the second plurality of images, and inspects the first and the second inspection area based on the first and the second plurality of images taken by the surface-side camera and the rear face-side camera, respectively, wherein when the surface-side camera takes the each of the first plurality of images, the controller causes the surface-side irradiator to start emitting the first light and causes the rear face-side irradiator to stop emitting the second light, and when the rear face-side camera takes the each of the second plurality of images, the controller causes the surface-side irradiator to stop emitting of the first light and causes the rear face-side irradiator to start emitting the second light, each of the first light and the second light is patterned light having a light intensity distribution of a stripe shape, and a first time period during which the each of the first plurality of images is taken and a second time period during which the each of the second plurality of images is taken are repeated alternately, wherein the first time period and the second time period each correspond to a predetermined phase of the patterned light.

\* \* \* \* \*